United States Patent [19]

Christenson et al.

[11] Patent Number: 4,992,106
[45] Date of Patent: Feb. 12, 1991

[54] NOVEL OXO-IONOL CARBONATES USEFUL AS TOBACCO FLAVORANTS

[75] Inventors: Philip A. Christenson, Midland Park, N.J.; Robert G. Eilerman, Merrick; Brian J. Drake, Clifton, both of N.Y.

[73] Assignee: BASF Corporation, Clifton, N.J.

[21] Appl. No.: 328,054

[22] Filed: Mar. 23, 1989

Related U.S. Application Data

[62] Division of Ser. No. 159,252, Feb. 23, 1988, Pat. No. 4,827,210.

[51] Int. Cl.$^5$ .................... A24B 3/12; A24B 15/30
[52] U.S. Cl. ................................................ 131/276
[58] Field of Search ........................................ 131/276

[56] References Cited

U.S. PATENT DOCUMENTS

| | | |
|---|---|---|
| 3,342,186 | 9/1967 | Cook . |
| 3,419,543 | 12/1968 | Mold et al. . |
| 3,545,452 | 12/1970 | Johnson . |
| 4,021,480 | 5/1977 | Tenud . |
| 4,068,012 | 1/1978 | Hall et al. . |
| 4,175,569 | 11/1979 | Hall . |
| 4,311,718 | 1/1982 | Kaiser et al. . |
| 4,311,860 | 1/1982 | Krasnobajew . |
| 4,337,354 | 6/1982 | Cragoe, Jr. et al. . |
| 4,363,331 | 12/1982 | Kaiser et al. . |
| 4,390,556 | 6/1983 | Krasnabojew . |
| 4,403,686 | 10/1968 | Kilburn . |
| 4,654,169 | 3/1987 | Ochaner . |

FOREIGN PATENT DOCUMENTS

0175251 3/1986 European Pat. Off. .

OTHER PUBLICATIONS

D. L. Roberts and W. A. Rohde, "Isolation and Identification of Flavor Component of Burley Tobacco", Tobacco Science, 16:107–112 (1972).
E. Demole and D. Berthet, "A Chemical Study of Burley Tobacco Flavour (Nicotiana tabacum L.) I. Volatile to Mediium–Volatile Constituents (b.p. < 84°/0.001 Torr", Helv. Chim. Acta, 55:1866–1882 (1972).
A. J. Aasen et al., "Tobacco Chemistry 15 New Tobacco Constituents—the Structures of Five Isomeric Megastigmatrienones", Acta Chem. Scand., 26:2573–2576 (1972).
J. Schumacher and L. Vestal, "Isolation and Identification of Smoke Components of Turkish Tobacco", Tobacco Science, pp. 43–48, Apr. 26, (1974).
A. J. Aasen et al., Tobacco Chemistry 7, Structure and Synthesis of 3–Oxo–α–Ionol, a New Tobacco Constituent, Acta. Chem. Scand., 25:1481–1482 (1971).
A. J. Aasen et al., "Absolute Configuration of (9R)-9-Hydroxy-4,7Emegastigmadien-3-one (3-Oxo-α–ionol)", Acta Chem. Scand., 27:2107–2114 (1973).

*Primary Examiner*—V. Millen
*Attorney, Agent, or Firm*—Richard L. Mayer

[57] ABSTRACT

Novel Oxo-ionol derivatives are described which have a but-1-en-3-ol carbonate side chain. These derivatives are stable tobacco enhancers which impart a slight hay-like flavor to tobacco smoke.

2 Claims, No Drawings

NOVEL OXO-IONOL CARBONATES USEFUL AS TOBACCO FLAVORANTS

This application is a division of application Ser. No. 159,252, filed Feb. 23, 1988, now U.S. Pat. No. 4,827,210.

BACKGROUND OF THE INVENTION

Megastigmatrienone (3,5,5-trimethyl-4-(2-butenylidene)-cyclohex-2-en-1-one, as a mixture of isomers) 1 is a component of Burley as well as Turkish and Greek tobaccos (See D. L. Roberts and W. A. Rhode, *Tobacco Science*, 1972, 16, 107; E. Demole and D. Berthet, *Helv. Chim. Acta*, 1972, 55, 1866; A. J. Aasen, B. Kimland, S. Almqvist and C. R. Enzell, *Acta. Chem. Scand.*, 1972, 26, 2573; and J. W. Schumacher and L. Vestal, *Tobacco Science*, 1974, 43) and is known to make an important contribution to the overall flavor character of tobacco.

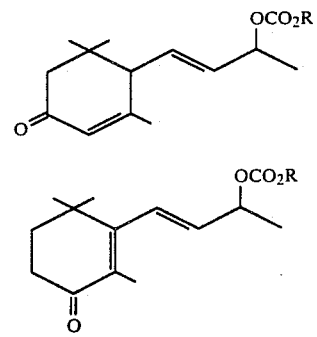

Megastigmatrienone 1 can be considered a dehydration product of 3-oxo-α-ionol 2, also a constituent of tobacco (see A. J. Aasen, B. Kimland and C. R. Enzell, *Acta Chem. Scand.*, 1971, 25, 1481). Glycosidyl derivatives of 2 have been described as useful smoke flavoring compositions (see R. C. Anderson, D. M. Gunn and J. A. Andrew, Ger. Offen. 2,634,304). Recently, R. Kaiser (Eur. Pat. Appl. 175, 251) has disclosed various esters of oxo-ionols of formula 3 as useful tobacco flavorants.

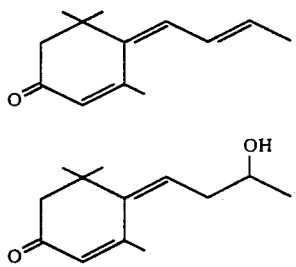

R is $C_1$-$C_{18}$ alkyl; Z is oxo and ⟿ indicates a single or double bond.

A problem associated with the use of megastigmatrienone 1, however, is its tendency to polymerize making it difficult to store, transport and formulate.

SUMMARY OF THE INVENTION

Accordingly, it is an object of the invention to develop a tobacco flavorant that has little or no tendency to polymerize and will be easy to store, transport and formulate.

This and other objects are achieved by the present invention which is directed to tobacco flavorants formulated from oxo-ionol derivatives having formulas 4 and 5 wherein R is lower alkyl of 1 to 6 carbons.

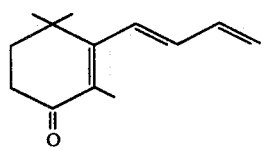

DETAILED DESCRIPTION OF THE INVENTION

Oxo-ionol derivatives of formulas 4 and 5 are stable at ambient temperature. This stability makes them useful in a variety of tobacco flavor systems. They impart no odor themselves to unsmoked tobacco, however upon smoking undergo a thermal elimination reaction producing in the smoke-stream megastigmatrienones 1 or 6, carbon dioxide and ethanol (in this case R = ethyl).

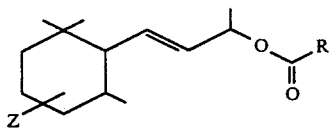

The oxo-ionol derivatives of the invention blend especially well with other flavors and upon smoking, function primarily as a flavor modifier or enhancer by rounding-out and smoothing the overall flavor. In addition, they impart a slight, desirable, hay-like note to the flavor and also mask papery off-notes and other less desirable notes present in the smoke-stream.

The oxo-ionol derivatives of the invention can be added to tobacco or applied to a smoking article or its component parts in amounts of 1 ppm to 1000 ppm. Preferably, the amount to be added is between 10 ppm and 500 ppm. The most preferred amount of additive is between 25 ppm and 150 ppm. Typically, they can be sprayed or dripped onto processed or dried whole tobacco or can be used in the form of a dip or solution into which the processed or raw tobacco is placed. The solutions useful for such dips, sprays and drips comprise the appropriate amount of oxo-ionol derivative and ethanol. Alternatively, the oxo-ionol derivatives can be applied neat to the finished tobacco product.

Oxo-ionol derivatives of formulas 4 and 5 can be prepared from the corresponding oxo-ionols 2 and 7 by standard methods known to those skilled in the art. (See C. A. Buehler and D. E. Pearson, "Survey of Organic Synthesis", Vol. 1, p. 802-822 (1970) and Vol. 2, p. 715-724 (1977), Wiley Interscience). For example, reaction of alcohols 2 or 7 with alkyl halo-formates in the presence of base provides compounds 4 and 5. Alternatively, transesterification reactions between alcohols 2 and 7 and dialkyl carbonates can be effected with various catalysts.

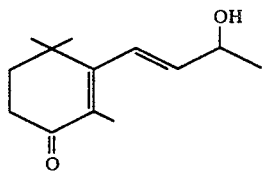

The following examples are set forth herein to illustrate methods of synthesis of the oxo-ionol derivatives of this invention and their use as tobacco flavorants. These examples are intended only to illustrate the embodiments of this invention and are in no way meant to limit the scope thereof.

EXAMPLE 1

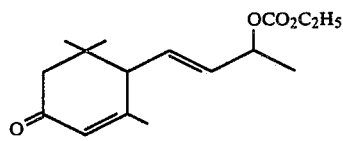

A solution of ethyl chloroformate (5.42g, 0.05 mol) in dichloromethane (10mL) was added dropwise over a 30 minute period to a cold (10° C.) solution of 3-oxo-α-ionol (5.20g, 0.025 mol, which may be prepared as described by A. J. Aasen, B. Kimland and C. R. Enzell in Acta Chem. Scand., 1973, 27, 2107-2114) and pyridine (3.96g, 0.05 mol) in dichloromethane (80mL). The mixture was stirred at 25° C. for 18 hours. Dichloromethane (100mL) was then added and the mixture washed with 5% phosphoric acid solution (3×100mL), saturated sodium bicarbonate solution until neutral and dried (sodium sulfate). Evaporation of solvent and chromatography of the residue followed by kugelrohr distillation (150° C. both temp. 0.5 mm) provided 4-(3-hydroxy-1-butenyl)-3,5,5,-trimethyl-2-cyclohexen-1-one ethyl carbonate (2.15g, GLC purity; 87%) $^1$H-NMR(CDCl$_3$) δ 0.97 (3H,s), 1.05 (3H, s), 1.31 (3H, t, J=7Hz), 1.41 (3H, d, J=7Hz), 1.92 (3H,s) 2.1-2.3 (2H,dd), 2.4-2.7 (1H,m), 4.25 (2H,q, J=7Hz), 5.0-5.4 (1H,m), 5.5-5.8 (2H,m), 5.95 (1H,s); OR (film) V$_{max}$ 2960, 1750, 1670, 1630, 1470, 1450, 1370, 1260 cm$^{-1}$; MS m/e 280, 224, 190,175, 134, 108.

EXAMPLE 2

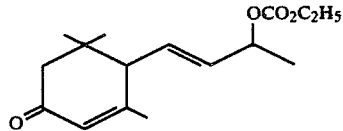

A mixture of 3-oxo-α-ionol (271g, 1.3 mol), diethyl carbonate (1.5L) and dibutyl tin oxide (16g) was heated at 105-115° C. for 40 hours. During the reaction, ethanol was removed by distillation. Distillation of the crude product provided 173.2g of material which GLC analysis indicated contained 51.5% of 4-(3-hydroxy1l-butenyl)-3,5,5-trimethyl-2-cyclohexen-1-one ethyl carbonate. Further purification by chromatography provided 72.56g of carbonate 4 (GLC purity; 85%).

EXAMPLE 3

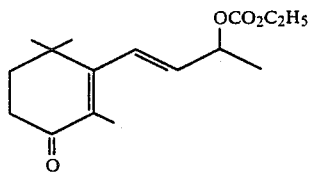

A solution of ethyl chloroformate (1.74g, 0.016 mol in dichloromethane (10mL) was added dropwise over a 1 hour period to a cold (5° C.) solution of 4-oxo-β-ionol (3.33g, 0.016 mol, which may be prepared as described by R. Kaiser and D. Lamparsky, Helv. Chim. Acta, 1978, 61, 2328-2335), pyridine (1.28g, 0.016 mol) and dichloromethane (30mL). After stirring the mixture at 5-10° C. for 2 hours it was added to ice water (20mL). The organic layer was washed with 5% phosphoric acid solution until neutral and dried over sodium sulfate. The solvent was removed and the residue chromatographed. Kugelrohr distillation (bath temp. 150° C., 0.5 mm) gave 2.0g (GLC purity; 85%) of 3-(3-hydroxy-1-butenyl)-2,4,4-trimethyl-2-cyclohexen-1-one ethyl carbonate. $^1$H-NMR (CDCl$_3$) δ 1.12 (6H,s), 1.35 (3H,d,J=7Hz), 1.40 (3H,t,J=7Hz), 1.77 (3H,s), 1.7-2.7 (4H,m), 4.20 (2H,q,J=7Hz), 4.8-5.4 (1H,m), 5.53 (1H,dd,J=16 and 6Hz), 6.31 (1H,d,J=16Hz); IR (film)v$_{max}$ 2960, 1745, 1665, 1460, 1440, 1365, 1250 cm$^{-1}$; MS m/e 280, 265, 236, 207, 191, 134.

EXAMPLE 4

Use in a Full Tar American Blend Cigarette

Cigarettes, typical of a full tar American blend, were produced using the following tobacco formulation:

| Ingredient | Parts by Weight |
| --- | --- |
| Flue Cured | 45 |
| Burley | 30 |
| Oriental | 20 |
| Flue Cured Stems | 5 |

To a portion of the above cigarettes was added by injection 4-(3-hydroxy-1-butenyl)-3,5,5-trimethyl-2-cyclohexen-1-one ethyl carbonate (4,R=ethyl) at a rate of 90 ppm. The experimental cigarettes were smoked and compared to the smoke from unflavored (control) cigarettes. The smoke from the experimental cigarettes was smoother, rounder and less irritating than that from the control cigarettes. No distinctive taste was noted from compound 4 (R=ethyl) on its own but its presence in the experimental cigarettes promoted balance in the taste of the smoke.

EXAMPLE 5

Use in a Charcoal Filter American Blend Cigarette

Cigarettes, typical of a charcoal filter American blend cigarette, were produced using the following tobacco formulation.

| Ingredient | Parts by Weight |
| --- | --- |
| Flue Cured | 50 |
| Burley | 26 |
| Oriental | 14 |

| Ingredient | Parts by Weight |
| --- | --- |
| Homogenized Leaf | 10 |

To a portion of the above cigarettes was added by injection 4-(3-hydroxy-1-butenyl)-3,5,5-trimethyl-2cyclohexen-1-one ethyl carbonate (4,R=ethyl) at a rate of 75 ppm. Upon smoking, the injected cigarettes have a substantially reduced charcoal off-taste which is found in the control cigarettes. Smoke from the injected cigarettes is cleaner with a reduced after taste.

EXAMPLE 6

Use in a Low Tar American Blend Cigarette

Cigarettes, typical of a low tar American blend cigarette, were produced using the following tobacco formulations:

| Ingredients | Parts by Weight |
| --- | --- |
| Expanded Flue Cured | 40 |
| Expanded Burley | 40 |
| Oriental | 15 |
| Expanded Flue Stems | 5 |

To a portion of the above cigarettes was added by injection 4-(3-hydroxy-1-butenyl)-3,5,5-trimethyl-2-cyclohexen-1-one ethyl carbonate (4, R=ethyl) at a rate of 125 ppm. When smoked, the injected cigarettes have an enhanced tobacco taste with a reduction of the papery taste characteristic noted in the smoke from the control cigarettes. In addition the injected cigarettes have a pleasant, hay-like taste which is compatible with the taste of the blend.

EXAMPLE 7

Use in a Full Tar American Blend Cigarette

Cigarettes, typical of a full tar American blend, were produced using the following tobacco formulation:

| Ingredients | Parts by Weight |
| --- | --- |
| Flue Cured | 45 |
| Burley | 30 |
| Oriental | 20 |
| Flue Cured Stems | 5 |

To a portion of the above cigarettes was added by injection 3-(3-hydroxy-1-butenyl)-2,4,4-trimethyl-2-cyclohexen-1one ethyl carbonate (5, R=ethyl) at the rate of 100 ppm. The injected cigarettes upon smoking displayed improved overall character of the smoke in comparison to the unflavored cigarettes.

We claim:

1. A tobacco composition comprising tobacco and from about the 1 to 1,000 ppm of an oxo-ionol derivative of the formula I or II

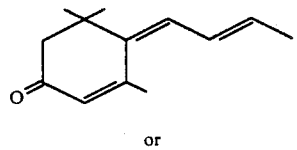

or

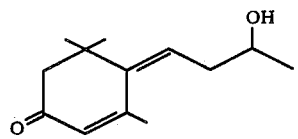

wherein R is lower alkyl of 1 to 6 carbons.

2. A tobacco composition according to claim 1 wherein R is ethyl.

* * * * *

UNITED STATES PATENT AND TRADEMARK OFFICE
CERTIFICATE OF CORRECTION

PATENT NO. : 4,992,106

DATED : February 12, 1991

INVENTOR(S) : Philip A. Christenson, et al.

It is certified that error appears in the above-identified patent and that said Letters Patent is hereby corrected as shown below:

In Claim 1, lines 4 to 6, delete

" 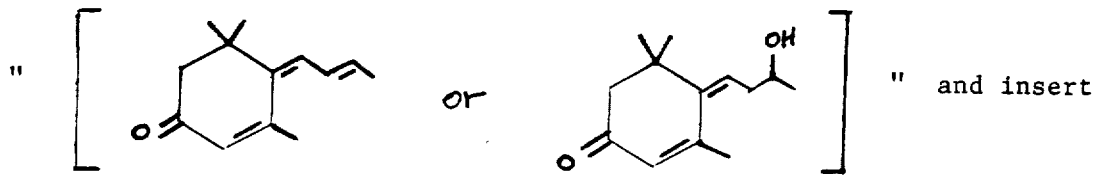 " and insert and insert the following:

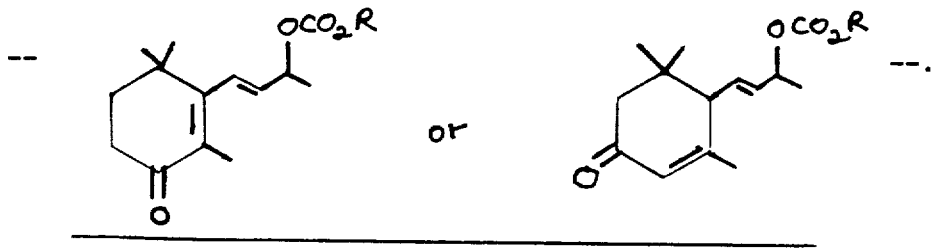 .

Signed and Sealed this

Sixth Day of October, 1992

Attest:

DOUGLAS B. COMER

Attesting Officer

Acting Commissioner of Patents and Trademarks